(12) United States Patent
Kelly et al.

(10) Patent No.: US 8,142,807 B2
(45) Date of Patent: Mar. 27, 2012

(54) BONE VOID FILLERS AND METHODS OF MAKING THE SAME

(75) Inventors: Robert James Kelly, Christchurch (NZ); Clive Marsh, Christchurch (NZ); Mohammed Azam Ali, Christchurch (NZ); Sigrid Edith Vorwerk, Boy of Island (NZ)

(73) Assignee: Keraplast Technologies, Ltd., San Antonio, TX (US)

( * ) Notice: Subject to any disclaimer, the term of this patent is extended or adjusted under 35 U.S.C. 154(b) by 499 days.

(21) Appl. No.: 11/987,939

(22) Filed: Dec. 6, 2007

(65) Prior Publication Data

US 2008/0206301 A1 Aug. 28, 2008

Related U.S. Application Data

(60) Provisional application No. 60/873,025, filed on Dec. 6, 2006, provisional application No. 60/924,171, filed on May 2, 2007.

(51) Int. Cl.
*A61F 2/00* (2006.01)

(52) U.S. Cl. ........................................ 424/423

(58) Field of Classification Search .................. None
See application file for complete search history.

(56) References Cited

U.S. PATENT DOCUMENTS

| | | |
|---|---|---|
| 2,591,945 A | 4/1952 | Koerner et al. |
| 3,567,363 A | 3/1971 | Wolfram |
| 3,619,116 A | 11/1971 | Saville |
| 3,644,084 A | 2/1972 | Hsiung et al. |
| 3,883,647 A | 5/1975 | Geller |
| 4,135,942 A | 1/1979 | Kikkawa |
| 4,172,073 A | 10/1979 | Kadri et al. |
| 4,407,793 A | 10/1983 | Akimova et al. |
| 4,775,620 A | 10/1988 | Cardiff et al. |
| 4,895,722 A | 1/1990 | Abe et al. |
| 4,904,602 A | 2/1990 | Pigiet et al. |
| 4,948,876 A | 8/1990 | Bore et al. |
| 4,969,880 A | 11/1990 | Zamierowski |
| 5,071,441 A | 12/1991 | Schnetzinger et al. |
| 5,154,916 A | 10/1992 | Arraudeau et al. |
| 5,358,935 A | 10/1994 | Smith et al. |
| 5,460,967 A | 10/1995 | Fink |
| 5,602,094 A | 2/1997 | Goddard |
| 5,763,583 A | 6/1998 | Arai et al. |
| 5,830,481 A | 11/1998 | Cauwet-Martin et al. |
| 5,932,552 A | 8/1999 | Blanchard et al. |
| 5,972,385 A | 10/1999 | Liu et al. |
| 6,039,962 A | 3/2000 | Cauwet-Martin et al. |
| 6,110,487 A | 8/2000 | Timmons et al. |
| 6,124,265 A | 9/2000 | Timmons et al. |
| 6,159,495 A | 12/2000 | Timmons et al. |
| 6,203,574 B1 | 3/2001 | Kawamura |
| 6,312,674 B1 | 11/2001 | Maubru et al. |
| 6,432,435 B1 | 8/2002 | Timmons et al. |
| 6,514,744 B2 | 2/2003 | Murata et al. |
| 6,544,548 B1 | 4/2003 | Siller-Jackson |
| 6,783,546 B2 | 8/2004 | Zucherman |
| 6,846,940 B2 | 1/2005 | Gaetani et al. |
| 7,169,896 B2 | 1/2007 | Schrooyen et al. |
| 7,297,342 B2 * | 11/2007 | Peplow et al. ............... 424/423 |
| 7,465,321 B2 * | 12/2008 | Kelly et al. ....................... 8/160 |
| 2001/0009675 A1 * | 7/2001 | Blanchard et al. ............ 424/445 |
| 2001/0018614 A1 | 8/2001 | Bianchi |
| 2002/0004068 A1 | 1/2002 | DiDrusco |
| 2002/0013408 A1 | 1/2002 | Rhee |
| 2002/0035046 A1 | 3/2002 | Lukenbach et al. |
| 2002/0183858 A1 | 12/2002 | Contiliano et al. |
| 2003/0035820 A1 | 2/2003 | Timmons et al. |
| 2003/0039676 A1 | 2/2003 | Boyce et al. |
| 2005/0053743 A1 * | 3/2005 | Kelly et al. ................... 428/40.1 |
| 2005/0232963 A1 * | 10/2005 | Peplow et al. ............... 424/423 |
| 2006/0165635 A1 | 7/2006 | Kelly et al. |
| 2006/0205652 A1 | 9/2006 | Zamora et al. |
| 2009/0062513 A1 * | 3/2009 | Kelly et al. ................... 530/350 |
| 2009/0069541 A1 * | 3/2009 | Kelly et al. ................... 530/357 |
| 2009/0111750 A1 * | 4/2009 | Kelly et al. ..................... 514/12 |

FOREIGN PATENT DOCUMENTS

| | | |
|---|---|---|
| CN | 1403643 | 3/2003 |
| CN | 1425813 | 6/2003 |
| EP | 0 628 573 A1 | 12/1994 |
| EP | 1 201 736 B1 | 4/2005 |
| FR | 1503640 | 12/1967 |
| FR | 2687577 A1 | 8/1993 |
| GB | 2 115 427 | 9/1983 |
| JP | 53-119900 | 10/1978 |
| JP | 54137064 | 10/1979 |
| JP | 63-301809 | 12/1988 |
| JP | 03-007596 | 1/1991 |
| JP | 03-294297 | 12/1991 |
| JP | 05-222100 | 8/1993 |
| JP | 05-320358 | 12/1993 |

(Continued)

OTHER PUBLICATIONS

MaClaren, John A., et al., "Wool Science The Chemical Reactivity of the Wool Fibre", pp. 12-14, 1981.

Hunter, Emma A.L., et al., "Cysteine and Methionin Supplementation Modulate the Effect of Tumor Necrosis Factor a on Protein Synthesis, Glutathione and Zinc Concentration of Liver and Lung in Rats Fed a Low Protein Diet", American Institute of Nutrition, vol. 124, No. 12, pp. 2319-2328, 1994.

Homandberg, G.A., et al., "Fibronectin Fragment Mediated Cartilage Chondrolysis. I. Suppression by Anti-Oxidants", Biochemica et Biophysica Acta, vol. 1317, pp. 134-142, 1996.

Parcell, Stephen, "Sulphur in Human Nutrition and Applications in Medicine", Alternative Medicine Review, vol. 7, No. 1, pp. 22-44, 2002.

(Continued)

*Primary Examiner* — Marcela M Cordero Garcia
(74) *Attorney, Agent, or Firm* — Vinson & Elkins LLP

(57) ABSTRACT

The invention relates to a material for use as bone void filler comprising soluble keratin protein. The material may be in the form of a putty, gel or emulsion. Additional components may be added to the material to improve handling characteristics and bone enhancement capabilities. The material may be formulated to serve as a suitable carrier for demineralized bone matrix. This invention also describes methods for making the material.

17 Claims, No Drawings

FOREIGN PATENT DOCUMENTS

| | | |
|---|---|---|
| JP | 06-100600 | 4/1994 |
| JP | 06-220713 | 8/1994 |
| JP | 06 192433 | 12/1994 |
| WO | WO 92/02238 | 2/1992 |
| WO | WO 98/51265 | 11/1998 |
| WO | WO 99/18922 | 4/1999 |
| WO | WO 99/19005 | 4/1999 |
| WO | WO 99/26570 | 6/1999 |
| WO | WO 00/23039 | 4/2000 |
| WO | WO 00/41739 | 7/2000 |
| WO | WO 00/70049 | 11/2000 |
| WO | WO 02/09659 | 2/2002 |
| WO | WO 03/011894 | 2/2003 |
| WO | WO 03/018673 | 3/2003 |
| WO | WO 03/103737 | 12/2003 |

OTHER PUBLICATIONS

Zafarullah, M., et al., "Molecular Mechanisms of N-Acetylcysteine Actions", Cellular and Molecular Life Sciences, vol. 60, No. 1, pp. 6-20, 2003.

Hummel, Klaus M., et al., "Cysteine Proteinase Cathepsin K mRNA Is Expressed in Synovium of Patients with Rheumatoid Arthritis and Is Detected at Sites of Synovial Bone Destruction", Journal of Rheumatology, vol. 25, No. 10, pp. 1887-1984, 1998.

Bradley, Helen, et al., "Sulfate Metabolism is Abnormal in Patients with Rheumatoid Arthiritis", Journal of Rheumatology, vol. 21, No. 7, pp. 1192-1196, 1994.

Wilkinson, L.J., et al., "Cysteine Diosygenase: Modulation of Expression in Human Cell Lines by Cytokines and Control of Sulphate Production", Toxicology in Vitro, vol. 16, pp. 481-483, 2002.

Tappaz, M.L., "Taurine Biosynthetic Enzymes and Taurine Transporter: Molecular Identification and Regulations", Neurochemical Research, vol. 29, No. 1, pp. 83-96, Jan. 2004.

Kontny, E., et al., "Impaired Generation of Taurine Chloramine by Synovial Fluid Neutrophils of Rheumatoid Arthritis Patients", Amino Acids, vol. 24, No. 4, pp. 415-418, 2002.

Roughley, Peter J., et al., "Cartilage Proteoglycans: Structure and Potential Functions", Microscopy Research and Technique, vol. 28, No. 5, pp. 385-397, 1994.

Rossi, Antonio, et al., "In Vitro Proteoglycan Sulfation Derived from Sulfhydryl Compounds in Sulfate Transporter Chondrodysplasias", Pediatric Pathology and Molecular Medicine, vol. 22, No. 4, pp. 311-321, 2003.

Kusche-Gullberg, Marion, et al., "Sulfotransferases in Glycosaminoglycan Biosynthesis", Current Opinion in Structural Biology, vol. 13, pp. 605-611, 2003.

Rath, Virginia L., "Sulfotransferase Structural Biology and Inhibitor Discovery", Drug Discovery Today, vol. 9, No. 23, pp. 1003-1011, Dec. 2004.

Venkatachalam, K.V., "Human 3'-phosphoadenosine 5'-phosphosulfate (PAPS) Synthase: Biochemistry, Molecular Biology and Genetic Deficiency", IUBMB Life, vol. 55, pp. 1-11, 2003.

Heyland, Daren K., et al., "Antioxidant Nutrients: A Systematic Review of Trace Elements and Vitamins in the Critically Ill Patient", Intensive Care Med., vol. 31, pp. 327-337, 2005.

Elsayed, Nabil M., "Antioxidant Mobilization in Response to Oxidative Stress: A Dynamic Environmental-Nutritional Interaction", Nutrition, vol. 17, pp. 828-834, 2001.

Serhan, Charles N., et al., "Resolution of Inflammation: The Beginning Programs the End", Nature Immunology, vol. 6, No. 12, pp. 1191-1197, Dec. 2005.

Henson, Peter M., "Dampening Inflammation", Nature Immunology, vol. 12, No. 12, pp. 1179-1182, Dec. 2005.

Verbruggen, G., "Chondroprotective Drugs in Degenerative Joint Diseases", Journal of Rheumatology, vol. 45, pp. 129-138, 2006.

Largo, R., et al., "Glucosomine Inhibits IL-1b-Induced NFkB Activation in Human Osteoarthritic Chondrocytes", OsteoArthritis and Cartilage, vol. 11, pp. 290-298, 2003.

Chan, P.S., et al., "Glucosamine and Chondroitin Sulfate Regulate Gene Expression and Synthesis of Nitric Oxide and Prostaglandin E2 in Articular Cartilage Explants", OsteArthritis and Cartilage, vol. 13, pp. 387-394, 2005.

Rassin, D.K., et al., "Nutritional Approaches to Improve Cognitive Development During Infancy: Antioxidant Compounds", Acta Paediatr Suppl., vol. 442, pp. 34-41, 2003.

Brugge, Karen L. et al., "The Role of Alterations in Free Radical Metabolism in Mediating Cognitive Impairments in Down's Syndrome", EXS, vol. 62, pp. 190-198, 1992.

Del Marmol, Veronique, et al., "Cysteine Deprivation Promotes Eumelanogenesis in Human Melanoma Cells", Journal of Investigative Dermatology, vol. 107, No. 5, pp. 698-702, 1996.

Smit, Nico P.M., et al., "Melanogenesis in Cultured Melanocytes Can Be Substantially Influenced by L-Tyrosine and L-Cysteine", Journal of Investigative Dermatology, vol. 109, No. 6, pp. 796-800, 1997.

Fujiwara, Y., et al., "Effect of Simultaneous Administration of Vitamin C, L-Cysteine and Vitamin E on the Melanogenesis", Biofactors, vol. 21, No. 104, pp. 415-418, 2004.

Kong, Kwang-Hoon, et al., "Expression and Characterization of Human Tyrosinase From a Bacterial Expression System", Comparative Biochemistry and Physiology, Part B, vol. 125, pp. 563-569, 2000.

Yamamura, Tatsuo, et al., "Antimelanogenic Activity of Hydrocoumarins in Cultured Normal Human Melanocytes by Stimulating Intracellular Glutathione Synthesis", Archives of Dermatological Research, vol. 294, No. 8, pp. 349-354m 2002.

Alonso, Laura C., et al., "Molecular Genetic and Endocrine Mechanisms of Hair Growth", Hormone Research, vol. 60, pp. 1-13, 2003.

Olney, J.W., et al., Brain Damage in Infant Mice Following Oral Intake of Glutamate, Aspartate or Cysteine, Nature, vol. 227, pp. 609-610, 1970.

Riise, G.C., "The Intrabronchial Microbial Flora in Chronic Bronchitis Patients: A Target for N-Acetylcysteine Therapy", European Respiratory Journal, vol. 7, pp. 94-101, 1994.

Grandjean, E.M., et al., "Efficacy of Oral Long-Term N-Acetylcysteine in Chronic Bronchopulmonary Disease: A Meta-Analysis of Published Double-Bline, Placebo-Controlled Clinical Trials", Clinical Therapy, vol. 22, pp. 209-221, 2000.

Hansen, N. C.G., et al., Orally Administered N-Acetylcysteine May Improve General Well-Being in Patients with Mild Chronic Bronchitis, Respitory Medicine, vol. 88, pp. 531-535, 1994.

Rasmussen, J.B., et al., Reduction in Days of Illness After Long-Term Treatment with N-Acetylcysteine Controlled-Release Tablets in Patients with Chronic Bronchitis, European Respitory Journal, vol. 1, pp. 351-355, 1988.

Parr, G.D., et al., Oral Fabrol (oral N-acetylcysteine) in Chronic Bronchitis, British Journal of Diseases of Chest, vol. 81, pp. 341-348, 1987.

Ardissino, D., et al., "Effect of Transdermal Nitroglycerin or N-acetylcysteine, or Both, in the Long-Term Treatment of Unstable Angina Pectoris", Journal of the American College of Caridiology, vol. 29, pp. 941-947, 1997.

Estensen, R.D., et al., "N-acetylcysteine Suppression of the Proliferative Index in the Colon of Patients with Previous Adenomatous Colonic Polyps", Cancer Letters, vol. 147, pp. 109-114, 1999.

Kinscherf, R., et al., Effect of glutathione Depletion and Oral N-acetylcysteine Treatment on CD4+ and CD8+ Cells. FASEB Journal, vol. 8, pp. 448-451, 1994.

Akerlund, et al., "Effect of N-acetylcystine (NAC) Treatment on HIV-1 Infection: A Double-Blind Placebo-Controlled Trial", European Journal of Clinical Pharmacology, vol. 50, pp. 457-461, 1996.

Zhang, Shumin, et al., "A Prospective Study of Plasma Total Cysteine and Risk of Breast Cancer", Epidemiology Biomarkers & Prevention, vol. 12, pp. 1188-1193, 2003.

James, L.P., et al., "Effect of N-Acetylcysteine on Acetaminophen Toxicity in Mice: Relationship to Reactive Nitrogen and Cytokine Formation", Toxicological Sciences, vol. 75, No. 2, pp. 458-467, 2003.

Shankar, K., et al., "Type 1 Diabetic Mice are Protected fro mAcetaminophen Hepatotoxicity", Toxicology Sciences, vol. 72, No. 2, pp. 220-234, 2003.

Goodman, M.T., Case-Control Study of Plasma Folate, Homocysteine, Vitamin B12, and Cysteine as Markers of Cervical Dysplasia, Cancer, vol. 89, No. 2, pp. 376-382, 2000.

Bernard, G.L. et al., "A Trial of Antioxidants N-Acetylcysteine and Procysteine in ARDS. The Antioxidant in ARDS Study Group", Chest, vol. 112, pp. 164-172, 1997.

Tepel, M., et al., "Prevention of Radiographic-Contrast-Agent-Induced Reductions in Renal Function by Acetylcysteine", New England Journal of Medicine, vol. 343, pp. 180-184, 2000.

Walters, M.T., et al., "A Double-Blind, Cross-Over, Study of Oral N-Acetylcysteine in Sjogren's Syndrome", Scand J. Rheumatol Suppl., vol. 61, pp. 253-258, 1986.

De Vries, N., et al., "N-acetyl-l-cysteine", Journal of Cellular Biochemistry Supplement, vol. 17F, pp. 270-277, 1993.

Beloqui, O., et al., "N-aceytl Cysteine Enhances the Response to Interferon-Alpha in Chronic Hepatitis C: A Pilot Study", Journal of Interferon Research, vol. 13, pp. 279-282, 1993.

Feghali, J.G., et al., "L-n-acetyl-cysteine Protection Against Cisplatin-Induced Auditory Neuronal and Hair Cell Toxicity", Laryngoscope, vol. 111, No. 7, pp. 1147-1155, 2001.

Balli, R., "Controlled Trial on the Use of Oral Acetylcysteine in the Treatment of Glue-Ear Following Drainage", European Journal of Respitory Diseases, vol. 61, Suppl. 111, pp. 159, 1980.

Yalcin, E. et al., "N-acetylcysteine in Chronic Blepharitis", Cornea, vol. 21, pp. 164-168, 2002.

De Flora, S., et al., "Mechanisms fo N-acetylcysteine in the Prevention of DNA Damage and Cancer, with Special Reference to Smoking-Related End-Points", Carcinogenesis, vol. 22, pp. 999-1013, 2001.

Connors, S.L., et al., "Secretin and Autism: The Role of Cysteine", Journal of the American Academy of Child and Adolescent Psychiatry, vol. 38, pp. 795-796, 1999.

Apple, S.K., et al., "Effect of Feather Meal on Live Animal Performance and Carcass Quality and Composition of Growing Finishign Swing", Journal of Animal Science, vol. 81, pp. 172-181, 2003.

Loy, T.W., et al., "Effects of Supplementation on Intake an Growth of Nursing Calves Grazing Native Range in Southeastern North Dakota", Journal of Animal Science, vol. 80, pp. 2717-2725, 2002.

Pohl, Thomas, "Concentration of Proteins and Removal of Solutes", Methods in Enzymology, vol. 182, pp. 68-83, 1990.

McNeil, Steven, "Heavy Metal Removal Using Wool Filters", Asian Textile Journal, pp. 88-90, May-Jun. 2001.

Fukatsu, K., "Degradation of Fe(III)—Wool Keratin Complex by Hydrogen Peroxide", Kumanoto Women's University, Kumamoto, Japan, Sen'i Gakkaishi (Fiber), vol. 46, No. 5. pp. 186-191 1990.

Thomas, Helga, et al., "In Vitro Reconstitution of Wool Intermediate Filaments", Int. J. Biol. Macromol., vol. 8, pp. 258-264, Oct. 1986.

Harrap, B.S., et al., "Soluble Derivatives of Feather Keratin", Biochem J., vol. 92, No. 8, pp. 8-18, 1964.

Swan, J.M., "The Reaction of Protein Thiol and Disulphide Groups with Cupric Sulphite Solutions", pp. 69-83, Sep. 1960.

Thomas, Helga, et al., "Experiments for the Isolation of Matrix Proteins of Wool in Disulphide Form", Melliand Textilberichte, pp. 297-300, Apr. 1983.

Goto M, Suyama K., "Occlusion of Transition Metal Ions by New Adsorbents Synthesized from Plant Polyphenois and Animal Fibrous Proteins", www.pubmed.gov, Dec. 18, 2006.

Mies, H.H., et al., "Chromatographic and Electrophoretic Investigation of the Properties of Unprotected Low-Sulphur Wool Kerateins", Journal of Chromatography, vol. 405, p. 365-370, 1987.

Pavlath, Attila E., et al., "Clarity of Films from Wool Keratin", Textile Res. J., vol. 69, No. 7, pp. 539-541, 1999.

Platt, A.J., et al., "A Comparative Study of Silicone Net Dressing and Paraffin Gauze Dressing in Skin-Grafted Sites", Burns, vol. 22, No. 7, pp. 543-545, 1996.

Valenta, Claudia, et al., "The Use of Polymers for Dermal and Transdermal Delivery", European Journal of Pharmaceutics and Biopharmaceutics, vol. 58, pp. 279-289, 2004.

Jonkman, Marcel F., et al., "New Method to Assess the Water Vapour Permeance of Wound Coverings", Biomaterials, vol. 9, pp. 263-267, May 1988.

Ming Yang, Jen, et al., "Properties of Chitosan Containing PP-g-AA-g-NIPAAm Bigraft Nonwoven Fabric for Wound Dressing", Journal of Membrane Science, vol. 243, pp. 1-7, 2004.

Freedman, Gordon, et al., "Practical Treatment of Pain in Patients with Chronic Wounds: Pathogenesis-Guided Management", The American Journal of Surgery, vol. 188, pp. 31S-35S, 2004.

Coderch, L., et al., "Chromatographic Characterization of Internal Polar Lipids from Wool", JAOCS, vol. 72, No. 6, pp. 715-720, 1995.

Coderch, L., et al., "Physicochemical Characteristics of Liposomes Formed with Internal Wool Lipids", JAOCS, vol., 73, No. 12, pp. 1713-1718, 1996.

Wertz, Philip W., et al., "The Composition of the Ceremides from Human Stratum Corneum and from Comedones", The Journal of Investigative Dermatology, vol. 84, No. 5, pp. 410-412, 1985.

Matsumoto, Kiyoichi, et al., "Studies on Regenerated Protein Fibers, III. Production of Regenerated Silk Fibroin Fiber by the Self-Dialyzing Wet Spinning Method", Journal of Applied Polymer Science, vol. 60, pp. 503-511, 1996.

Yang, Yiqi, et al., "Formaldehyde-Free Zein Fiber-Preparation and Investigation", Journal of Applied Polymer Science, vol. 59, pp. 433-441, 1996.

Cates, David M., et al., "Preparation and Properties of Fibers Containing Mixed Polymers III. Polyacrylonitrile-Silk Fibers", Journal of Polymer Science, vol. 21, No. 97, pp. 125-138, 1956.

Schimpf, Warren C., "Fibers from Regenerated Collagen", Ind. Eng. Chem., Prod. Res. Dev., vol. 16, No. 1, pp. 90-92, 1977.

Sastry, T.P., et al., "Graft Copolymerization of Feather Keratin Hydrolyzate: Preparation and Characterization", Journal of Polymer Materials, vol. 14, No. 2, pp. 177-181, 1997.

Tanabe, Toshizumi, et al., "Preparation and Characterization of Keratin-Chitosan Composition Film", Biomaterials, vol. 23, pp. 817-825, 2002.

Yamauchi, Kiyoshi, et al., "Cultivation of Fibroblast Cells on Keratin-Coated Substrata", J. Biomater Sci. Polymer Edn., vol. 9, No. 3, pp. 259-270, 1998.

Gillespie, J. Morton, "The Structural Proteins of Hair: Isolation, Characterization, and Regulation of Biosynthesis", Biochemistry and Physiology of the Skin, pp. 475-510, 1983.

Marshall, R.C., et al., "Structure and Biochemistry of Mammalian Hard Keratin", Electron Micros. Rev., vol. 4, pp. 47-83, 1991.

Milgram, Norton W., et al., "Landmark Discrimination Learning in the Dog: Effects of Age, and Antioxidant Fortified Food, and Cognitive Strategy", Neuroscience and Biobehavioral Reviews, vol. 26 pp. 679-695, 2002.

Kazunori, Katoh, et al., "Preparation and Properties of Keratin-Poly(vinyl alcohol) Blend Fiber", Journal of Applied Polymer Science, vol. 91, pp. 756-762, 2004.

Gorman, Jessica, "Materials Take Wing: What to Do With 4 Billion Pounds of Feathers?", Science News, Feb. 23, 2002, vol. 161, p. 102(2).

* cited by examiner

BONE VOID FILLERS AND METHODS OF MAKING THE SAME

This application claims the benefit of priority of provisional application No. 60/873,025, filed Dec. 6, 2006 and provisional application No. 60/924,171, filed May 2, 2007.

FIELD OF THE INVENTION

The present invention is directed to materials comprising soluble keratin that serve to fill bone voids, deliver beneficial components to bone voids and enhance bone formation. The material may be a putty that comprises soluble keratin and is moldable and capable of filing irregular shaped void spaces. The material may also be a gel that comprises soluble keratin and is injectable and capable of being injected directly into a defect site and enhancing bone formation. The material may also be an emulsion comprising soluble keratin. In one aspect of the present invention, the putty, gel and emulsion are formulated to be suitable carriers for demineralized bone matrix. Each of the materials may also further comprise additional components, such as ceramic material, growth factors, stem cells, drugs, etc., to improve, e.g., handling characteristics of the material and the ability to enhance bone formation. The present invention is also directed to a method of preparing each of the materials.

BACKGROUND OF THE INVENTION

Genetics, surgical events, traumatic events and cancerous events are just a few of the examples that may lead to voids or cracks in bone. In certain cases, these bone voids may be left unfilled since the void causes no physical harm to the individual. However, in such cases, the individual may be left feeling awkward due to a hole left in, e.g., their skull following a surgical procedure. In other instances, it is necessary to fill the void because, e.g., the presence of the void causes a degree of instability in the surrounding area. In these cases, the voids are filled with a material that helps to provide the desired stability.

A preferable material for filling both those voids which require filling for the physical health of the individual and those that do not should be capable of filling the void to provide needed stability and also aid in the formation of new bone that eventually replaces the bone void filler and eliminates the void permanently. Thus, a preferable material should be osteogenic (bone forming), osteoinductive (stimulate bone forming cells) and osteoconductive (provide environment for cells to form new bone).

It is also beneficial if the material is capable of effectively serving as a carrier of other beneficial agents, e.g., an agent that will enhance bone formation when delivered to the bone defect or void.

In addition, the material should be sterile, easy to handle, stay together when shaped and stay together when rinsed with saline. The material may be moldable or non-moldable, depending on the application, and when moldable the material should be capable of remembering its shape.

However, to date, none of the existing bone void filling materials accomplishes all of these desirable characteristics.

SUMMARY OF THE INVENTION

It has been discovered by the inventors of the present application that different forms of a material comprising soluble keratin protein provide a bone void filler that possesses many, if not all, of the desirable attributes discussed above for a bone void filler. The material may be in the form of a putty comprising soluble keratin protein, a gel comprising soluble keratin protein, or an emulsion comprising soluble keratin protein. These materials serve to fill a bone void, provide a degree of stability to the bone void, enhance bone formation and/or provide beneficial agents to the defect site. Methods of forming the materials are also disclosed herein.

The first embodiment of the present invention is directed to a putty for use as bone void filler comprising soluble keratin protein. The soluble keratin protein may be reduced keratin, oxidized keratin or S-sulfonated keratin. The putty may optionally include autologous bone chips, plasticizers, ceramics, growth factors and other components to improve the handling characteristics and/or enhance bone formation capabilities of the putty.

The second embodiment of the present invention is directed to a gel for use as a bone void filler comprising soluble keratin protein. The soluble keratin protein may be reduced keratin, oxidized keratin or S-sulfonated keratin. The gel may optionally include autologous bone chips, plasticizers, ceramics, growth factors and other components to improve the handling characteristics and/or bone enhancing capabilities of the gel.

The third embodiment of the present invention is directed to an emulsion for use as a bone void filler comprising soluble keratin protein dispersed in oil. The soluble keratin protein may be reduced keratin, oxidized keratin or S-sulfonated keratin. The emulsion may optionally include other components to improve the handling characteristics and/or bone enhancing capabilities of the putty.

The fourth embodiment of the present invention is directed to a putty that, in addition to serving as a bone void filler, is a suitable carrier for demineralized bone matrix. The putty comprises soluble keratin protein. The soluble keratin protein may be reduced keratin, oxidized keratin or S-sulfonated keratin.

The fifth embodiment of the present invention is directed to a gel that, in addition to serving as a bone void filler, is a suitable carrier for demineralized bone matrix. The gel comprises soluble keratin protein. The soluble keratin protein may be reduced keratin, oxidized keratin or S-sulfonated keratin.

The sixth embodiment of the present invention is directed to an emulsion that, in addition to serving as bone void filler, is a suitable carrier for demineralized bone matrix.

The seventh embodiment of the present invention is directed to a method for preparing the putty of the first embodiment. The method comprises the steps of preparing an aqueous solution of soluble keratin protein and then mixing the aqueous solution with insoluble keratin. Other optional components may be added to improve handling characteristics and enhance bone growth.

The eighth embodiment of the present invention is directed to a method for preparing the gel of the second embodiment. The method comprises the steps of preparing an aqueous solution of soluble keratin protein and then and then mixing the aqueous solution with an insoluble keratin. Other optional components may be added to improve handling characteristics and enhance bone growth.

The ninth embodiment of the present invention is directed to a method for preparing the emulsion of the third embodiment.

The tenth embodiment of the present invention is directed to a method for preparing the putty of the fourth embodiment. The method comprises the steps of preparing an aqueous solution of soluble keratin protein, and then mixing the aqueous solution insoluble keratin and demineralized bone matrix.

The eleventh embodiment of the present invention is directed to a method for preparing the gel of the fifth embodiment. The method comprises the steps of preparing an aqueous solution of soluble keratin protein and then mixing the aqueous solution with insoluble keratin and demineralized bone matrix.

The twelfth embodiment of the present invention is directed to a method for preparing the emulsion of the sixth embodiment.

DETAILED DESCRIPTION OF THE PREFERRED EMBODIMENTS

In a first embodiment of the present invention, a putty for use as a bone void filler is disclosed. The putty comprises soluble keratin protein, and may further comprise additional components for improving handling characteristics and/or bone enhancement.

By putty it is meant a substance having a uniform consistency that is solid but moldable and pliable. The putty of the instant invention may be molded and shaped. Preferably, the putty is capable of remembering its shape.

Keratin is a family of proteins characterized by a high degree of the amino acid cystine, which imparts a high degree of crosslinking to keratin proteins through disulfide links. Keratin proteins are also highly ordered proteins providing a fundamental structural role to many biological tissues. The fibrous nature of keratins provides a good basis for constructing ordered networks and robust materials. Keratin proteins are particularly well suited to the formulation of viscous liquids and putties, due to the ordered fibrous proteins and the tendency for the fibrous proteins to interact. Furthermore, the occurrence of disulfide crosslinks provides a degree of resiliency to enzymatic degradation within the body, allowing any material delivered in the keratin to be maintained at a particular site for a controllable period of time.

Keratin promotes new bone growth, can be given varying degrees of moldability, and stays together when handled and when in saline. Keratin remembers shape, can be sterilized and is a low disease risk. Accordingly, keratin is especially suitable for use as a bone void filler that encourages increased bone growth.

Because keratin is naturally insoluble, keratin must be chemically modified to produce soluble keratin protein. Any keratin modified to be soluble may be used in the present invention, just as any method for solubilizing keratin known in the art may be used to provide a soluble keratin for use in the present invention.

In one aspect of the first embodiment, the soluble keratin is S-Sulfonated keratin protein. S-Sulfonated keratin refers to keratin protein that undergoes a process wherein the disulfide bonds between cystine amino acid in keratin protein are reversibly modified to create polar functional groups that allow for controlled re-introduction of the natural disulfide crosslinks originally present in the keratin protein. The mechanism for modifying the cystine disulfide bond to cysteine S-sulfonate is summarized as follows, wherein K is keratin:

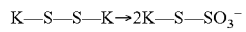

S-sulfonated keratin protein may be prepared by a variety of methods, including those described in WO 2003/011894, incorporated herein by reference.

As shown above, S-sulfonated keratins have cysteine/cystine present predominantly in the form of S-sulfocysteine. This highly polar group imparts a degree of solubility to proteins. Whilst being stable in solution, the S-sulfo group is a liable cysteine derivative, highly reactive towards thiols, such as cysteine, and other reducing agents. Reaction with reducing agents leads to conversion of the S-sulfo cysteine group back to cystine. S-sulfo cysteine is chemically different from cysteic acid, although both groups contain the $SO_3^-$ group. Cysteic acid is produced irreversibly by the oxidation of cysteine or cystine and once formed cannot form disulfide crosslinks back to cysteine. S-sulfocysteine is reactive towards cysteine and readily forms disulfide crosslinks.

The soluble keratin of the first embodiment may also be oxidized keratin. Oxidized keratins are produced as a result of exposing insoluble keratins to oxidizing agents, resulting in the conversion of cystine to cysteic acid and the keratin being converted to a soluble form. As a result of this, oxidized keratins are suitable for the formulation of putty comprising soluble keratin for use in bone healing disclosed herein.

The soluble keratin of the first embodiment may also be reduced keratin. Reduced keratins are produced as a result of exposing insoluble keratins to reducing agents, such as thiols, phosphines or other similar reducing agents. This converts the cystine present to cysteine or an alternative derivative, cleaving the crosslinks and converting the insoluble keratin into a soluble form. In this form, reduced keratins are soluble and a suitable basis from which to formulate putties for use in bone healing such as those described herein.

In the first embodiment, the soluble keratin protein is from 4-25% by weight of the putty of the first embodiment and is most preferably 13.5% by weight of the putty.

The keratin protein made soluble by one of the aforementioned mechanisms is preferably a keratin protein fraction. Keratin protein fractions are distinct groups from within the keratin protein family, and include intermediate filament proteins, high sulfur proteins and high glycine-tyrosine proteins known in the art.

Intermediate filament proteins are a first type of keratin protein fraction and are described in detail by Orwin et al. (*Structure and Biochemistry of Mammalian Hard Keratin*, Electron Microscopy Reviews, 4, 47, 1991) and also referred to as low sulfur proteins by Gilliespie (Biochemistry and physiology of the skin, vol. 1, Ed. Goldsmith Oxford University Press, London, 1983, pp. 475-510). Key characteristics of intermediate filament protein family are molecular weight in the range 40-60 kD and a cysteine content (measured as half cystine) of around 4%.

The high sulfur protein family is another type of keratin protein fraction that is well described by Orwin and Gillispie in the same publications referenced above. This protein family has a large degree of heterogeity, but can be characterized as having a molecular weight in the range 10-30 kD and a cysteine content of greater than 10%. A subset of this family is the ultrahigh sulfur proteins, which can have a cysteine content of up to 34%.

The high glycine-tryosine protein family is still another type of keratin protein fraction that is well described by Orwin and Gillispie in the same publications referenced above. This family is also referred to as the high tyrosine proteins and has characteristics of a molecular weight less than 10 kD, a tyrosine content typically greater than 10% and a glycine content typically greater than 20%.

For the purpose of this invention, a "keratin protein fraction" is a purified form of keratin that contains predominantly, although not entirely, one distinct protein group as described above.

The soluble keratin protein of the first embodiment may also be intact. The term intact refers to proteins that have not been significantly hydrolysed, with hydrolysis being defined as the cleavage of bonds through the addition of water. Gillispie considers intact to refer to proteins in the keratinized polymeric state and further refers to polypeptide subunits which complex to form intact keratin in wool and hair. For purposes of this invention, intact refers to the polypeptide subunits described in Gillispie. These are equivalent to the keratin proteins in their native form without the disulfide crosslinks formed through the process of keratinization.

Intact keratin proteins and keratin protein fractions are discussed in greater detail in co-pending U.S. patent application Ser. No. 10/583,445, filed Jun. 19, 2006 and of which the entire application is hereby incorporated by reference.

The soluble keratin protein is preferably in a solution, the solution being any suitable solution for use in a bone healing, such as water. The water is preferably from 20 to 40% by weight of the putty and is most preferably 29.4% by weight of the putty.

The putty may further comprise insoluble keratin protein. The insoluble keratin protein thickens the putty to provide the proper consistency to the putty. As discussed above, the proper putty consistency is such that the material is solid, but moldable and pliable, and preferably capable of remembering its shape. The insoluble keratin protein is preferably crosslinked S-sulfonated keratin or lanthionized keratin.

In the case of S-sulfonated keratin protein, the conversion of the S-sulfonate form to the disulfide form is considered crosslinking and may be accomplished through application of reducing conditions, for example, by applying a thiol. The mechanism for reforming the crosslinks in S-sulfonated keratin protein may be summarized as follows, wherein K is keratin and R is a reducing agent:

$$K-S-SO_3^- + R-S^- \rightarrow K-S-S-R + SO_3^{2-}$$

$$K-S-S-R + R-S^- \rightarrow K-S-+R-S-S-R$$

$$K-S-SO_3^- + K-S^- \rightarrow K-S-S-K + SO_3^{2-}$$

Lantionization refers to the transformation of cystine bonds to lanthionine bonds. Lanthionine bonds are a monosulfide analog of cystine.

When present in the putty, the insoluble keratin protein may be from 15 to 60% by weight of the putty of the first embodiment, and is most preferably 45.1% by weight of the putty.

Other components affecting the consistency of the putty may be added, including plasticizers (such as glycerol), vegetable oil and cellulose derivatives (such as alkylated cellulose and methyl cellulose). These components may be added to the putty in any suitable amount, but are preferably added in small amounts, e.g., 0 to 3% by weight of the putty. The putty may also comprise preservatives, for example a mixture of paraben and phenoxyethanol, in a small amount (i.e., less than 1% by weight of the putty).

The putty of the first embodiment may comprise still further components which aid in improving the rate of bone growth and/or aid in improving the physical characteristics of the putty.

For example, the putty may also comprise ceramic material. Keratin and ceramic compositions have been demonstrated as providing a favorable environment for the healing of bone. By providing a matrix rich in both proteins and the minerals required by healing bone, positive healing outcomes have been observed on the inclusion of keratin-ceramic compositions at sites of bone injury, see for example Kelly et al., WO 03/103737 A1.

The ceramic material may be any ceramic that is suitable for use in a bone healing composition. Suitable ceramics include glass ceramics and calcium phosphates, such as octacalcium phosphate, apatites, hydroxyapatite, carbonate apatite, whitlockites, β-tricalcium phosphate and α-tricalcium phosphate and calcium sulphate. In a preferred embodiment of the present invention, the ceramic material is calcium sulphate, calcium phosphate, tricalcium phosphate or hydroxyapatite. Ceramic material is used in an amount such as to provide useful physical characteristics, such as improved handling, while not changing the bone healing characteristics of the putty. Ceramic may be added to the putty in a range of from 0 to 15% by weight of the putty, and most preferably 10% by weight of the putty.

Growth factors may also be added to the putty described above. Specifically, growth factors known to promote bone growth may be used. Examples of suitable bone growth factors include bone morphogenetic protein (BMP), epidermal growth factor (EGF) and vascular endothelial growth factor (VEGF), including as either protein or encoding DNA forms. With respect to BMP's, these growth factors function to induce cartilage and bone formation, belong to the Transforming Growth Factor-beta (TGF-beta) family and are commercially available from companies such as Antigenix America, Huntington Station, N.Y.

Antioxidants may also be added to the putty of the first embodiment. Suitable antioxidants include, but are not limited to, alcohols such as sorbitol, sulfur compounds, such as glutathione and n-acetyl cysteine, free radical scavengers, enzymes such as superoxide dismutase, glutathione peroxidise, beta-carotene, lycopene, and vitamins A, C and E.

Autograft and allograft material may also be added to the putty of the first embodiment. Suitable autograft materials include, but are not limited to, cortical or cancellous bone taken from long bones. Suitable allograft materials include, but are not limited to, demineralized bone matrix.

In a specific example of autograft material used in the bone putty described above, cancellous bone tissue and cortical bone tissue are used in the bone putty. The cancellous and cortical bone tissue is retrieved from a bone bank, such as the NSW Bone Bank located in Kogarah, NSW, Australia, and is fresh frozen. The tissue is then prepared in aseptic conditions in a clean room and sterilized by gamma irradiation. Any suitable amount of the mixture of cortical and cancellous bone may be used in combination with the putty of the first embodiment. The cortical and cancellous bone chips may also be mixed with the recipients own bone chips during surgery.

Stem cells and cell therapies may also be added to the putty of the first embodiment. Any stem cells known to be capable of acting to form bone or other cells may be included in the putty of the first embodiment. This includes media to support growth of these cells. The putty may also include dendritic and other therapeutic cell therapies.

Drugs may also be added to the putty of the first embodiment. Examples of drugs suitable for use in the putty include, but are not limited to, antibiotics, such as penicillin and cephalosporin, bone growth/anti-osteoporosis agents such as parathyroid hormone, statins and Teriparatide, and agents to treat bone disease.

DNA and RNA based therapies may also be added to the putty of the first embodiment. DNA and RNA based therapies suitable for use in the putty of the first embodiment include, but are not limited to, RNA molecules, anti-sense nucleotides, and copy DNA encoding bone active proteins.

Antibodies may also be added to the putty of the first embodiment. Antibodies suitable for use in the putty of the first embodiment include, but are not limited to, antibodies that may be positive or negative effectors of bone growth. For example, antibody against BMP antagonist will stimulate bone growth and would be suitable for use in the bone void putty of the first embodiment.

The above described additional components of the putty may be present in the putty in any amount that will allow the added component to have a beneficial effect on enhancing bone growth or providing improved physical stability or handling characteristics, while not significantly altering the stability or form of the putty material.

When applying the putty as described above to a bone void, autologous bone chips may be added to the putty of the first embodiment before the putty is inserted in a bone void. The autologous bone chips added to the putty prior to application are preferably added at a rate of up to 0.5 grams of bone chips per 1 gram of putty.

In a second embodiment of the present invention, a gel for use as a bone void filler is disclosed. The gel comprises soluble keratin protein, and may further comprise additional components for improving handling characteristics and/or bone enhancement.

In one aspect of the second embodiment, the soluble keratin is S-sulfonated keratin protein as described above. The soluble keratin may also be reduced keratin, or oxidized keratin as described above.

In the second embodiment, the soluble keratin protein may be from 4-25% by weight of the gel.

Also as described above with respect to the first embodiment, the keratin protein made soluble by one of the aforementioned mechanisms is preferably a keratin protein fraction. The soluble keratin protein of the second embodiment may also be intact as described above with respect to the first embodiment.

The soluble keratin protein is preferably in a solution, the solution being any suitable solution for use in a bone healing, such as water. The water is preferably from 20 to 50% by weight of the gel.

As with the putty of the first embodiment, the gel of the second embodiment may further comprise insoluble keratin protein, which is preferably crosslinked S-sulfonated keratin or lanthionized keratin. The insoluble keratin protein may be from 10 to 60% by weight of the gel.

Other components affecting the consistency of the gel may be added, including plasticizers (such as glycerol), vegetable oil and cellulose derivatives (such as alkylated cellulose and methyl cellulose). Theses components are preferably added in small amounts, e.g., 0 to 3% by weight of the gel. The gel may also comprise preservatives, for example a mixture of paraben and phenoxyethanol, in a small amount (i.e., less than 1% by weight of the gel).

The gel of the second embodiment may comprise still further components which aid in improving the rate of bone growth and/or aid in improving the physical characteristics of the gel. For example, the gel may also comprise ceramic material as discussed above in the first embodiment, and/or growth factors, antioxidants, autograft and allograft material, stem cells and cell therapies, drugs, DNA and RNA based therapies and antibodies as discussed above in the first embodiment.

When applying the gel as described above to a bone void, autologous bone chips may be added to the gel of the second embodiment before the gel is inserted in a bone void. The autologous bone chips added to the gel prior to application are preferably added at a rate of up to 0.5 grams of bone chips per 1 gram of gel.

In a third embodiment of the present invention, an emulsion for use as a bone void filler is disclosed. The emulsion comprises soluble keratin protein suspended in oil.

The emulsion is believed to be a beneficial form of bone void filler because it allows for the material to be sterilized without allowing cross-linking. Because the pockets of keratin are predominantly separated by the oil in the emulsion, the keratin cannot crosslink when sterilized. By preventing cross-linking, the keratin component is less likely to crumble and therefore has better physical characteristics as a bone void filler.

The keratin component of the emulsion is identical to the keratin described above with respect to the putty and gel. That is to say, the emulsion comprises soluble keratin protein, which may be S-sulfonated, oxidized, or reduced keratin and the soluble keratin is preferably intact keratin protein fraction, such as intact intermediate filament keratin protein.

As described above with respect to the putty and gel, the soluble keratin protein of the emulsion is preferably in a solution, the solution being any suitable solution for use in a bone void filler, such as water. The aqueous solution may be any ratio of soluble keratin to solution suitable for preparing an aqueous solution. Controlling the amount and concentration of keratin in solution plays a part in the physical characteristics of the composition, such as the fluidity.

Prior to being added to the oil component of the emulsion, insoluble keratin may be further added to the aqueous solution of soluble keratin protein to regulate the viscosity prior to sterilization. Crosslinked S-sulfonated keratin or lanthionized keratin are two types of insoluble keratin which may be used.

Also as described in detail above, the emulsion may further comprise additional components to improve the handling characteristics of the emulsion and/or bone enhancement. Thus, as with the putty and gel, the emulsion may further comprise plasticizers, ceramic material, antioxidants, autograft, allograft, cell therapies, stem cells, drugs, DNA-based therapies, RNA-based therapies, antibodies, and/or preservatives.

The oil component of the emulsion may comprise any suitable oil, for example, castor oil or mineral oil.

In a fourth embodiment of the present invention, putty for use as a bone void filler and which is a suitable carrier for demineralized bone matrix is disclosed. The putty comprises soluble keratin protein, and may further comprise additional components for improving handling characteristics and/or bone enhancement.

The soluble keratin may be S-sulfonated keratin, reduced keratin, or oxidized keratin as described above with respect to the first embodiment.

In the fourth embodiment, the soluble keratin protein is from 15-45% by weight of the putty and is most preferably 28.1% by weight of the putty.

The keratin protein made soluble by one of the aforementioned mechanisms is preferably a keratin protein fraction. The keratin protein fraction is preferably intermediate filament protein, high sulfur protein or high glycine-tyrosine protein. The soluble keratin protein is also preferably intact as described above.

The soluble keratin protein is preferably in a solution, the solution being any suitable solution for use in a bone healing, such as water. The water is preferably from 25 to 75% by weight of the putty and is most preferably 66% by weight of the putty.

The putty may further comprise insoluble keratin protein, which thickens the putty to an appropriate consistency. The insoluble keratin protein is preferably crosslinked S-sulfonated keratin or lanthionized keratin as discussed in greater detail above.

The insoluble keratin protein may be from 0 to 5% by weight of the putty, and is most preferably 1.9% by weight of the putty.

Other components affecting the consistency of the putty may be added, including plasticizers (such as glycerol), vegetable oil and cellulose derivatives (such as alkylated cellulose and methyl cellulose). Theses components may be added to the putty in a suitable amount, but are preferably added in small amounts, e.g., 0 to 5% by weight of the putty. The putty may also comprise preservatives, for example a mixture of paraben and phenoxyethanol, in a small amount (i.e., less than 1% by weight of the putty).

The putty of the fourth embodiment may comprise still further components which aid in improving the rate of bone growth and/or aid in improving the physical characteristics of the putty. For example, the putty may also comprise ceramic material as discussed above in the first embodiment, and/or growth factors, antioxidants, autograft and allograft material, stem cells and cell therapies, drugs, DNA and RNA based therapies and antibodies as discussed above in the first embodiment.

The above described additional components of the putty may be present in the putty in any amount that will allow the added component to have a beneficial effect on enhancing bone growth and/or providing improved physical stability or handling characteristics, while not significantly altering the stability or form of the putty material.

As noted above, the putty of the fourth embodiment is a suitable carrier for demineralized bone matrix. Demineralized bone matrix, or DBM, is produced from banked bone taken from cadavers. DBM is usually available in a lyophilized or freeze-dried and sterile form, such as cubes, shavings, or powder. This allows the DBM to have a longer storage life. Commercially available demineralized bone matrix may be purified by a variety of procedures for the removal of non-protein components and can be obtained from various companies such as Citagenix, Inc., Quebec, Canada.

The source of the demineralized bone matrix is not limited, and may be from human bone or any socially or economically important animal species. In one aspect of the fourth embodiment, the demineralized bone matrix may be human, rat, cow, horse, pig, dog, cat or sheep demineralized bone matrix.

Demineralized bone is preferably added to the putty of the fourth embodiment in an amount of up to 0.55 grams per 1 gram of putty, and is preferably added in an amount of 0.3 grams per 1 gram of putty. After adding an appropriate amount of DBM to the putty of the fourth embodiment, the putty is suitably moldable so that the putty may adapt to the shape of the bone defect site to more effectively aid in bone healing.

In a fifth embodiment of the present invention, gel for use as a bone void filler and which is a suitable carrier for demineralized bone matrix is disclosed. The gel comprises soluble keratin protein, and may further comprise additional components for improving handling characteristics and/or bone enhancement.

The soluble keratin may be S-sulfonated keratin, reduced keratin, or oxidized keratin as described above with respect to the first embodiment.

In the fifth embodiment, the soluble keratin protein is from 10-35% by weight of the gel and is most preferably 21.3% by weight of the gel.

The keratin protein made soluble by one of the aforementioned mechanisms is preferably a keratin protein fraction. The keratin protein fraction is preferably intermediate filament protein, high sulphur protein or high glycine-tyrosine protein. The soluble keratin protein is also preferably intact as described above.

The soluble keratin protein is preferably in a solution, the solution being any suitable solution for use in a bone healing, such as water. The water is preferably from 30 to 80% by weight of the gel and is most preferably 72.8% by weight of the gel.

The gel may further comprise insoluble keratin protein, which thickens the gel to an appropriate consistency. The insoluble keratin protein is preferably crosslinked S-sulfonated keratin or lanthionized keratin as discussed in greater detail above.

The insoluble keratin protein may be from 0 to 5% by weight of the gel, and is most preferably 1.9% by weight of the gel.

Other components affecting the consistency of the gel may be added, including plasticizers (such as glycerol), vegetable oil and cellulose derivatives (such as alkylated cellulose and methyl cellulose). Theses components may be added to the gel in a suitable amount, but are preferably added in small amounts, e.g., 0 to 5% by weight of the gel. The gel may also comprise preservatives, for example a mixture of paraben and phenoxyethanol, in a small amount (i.e., less than 1% by weight of the gel).

The gel of the fifth embodiment may comprise still further components which aid in improving the rate of bone growth and/or aid in improving the physical characteristics of the gel. For example, the gel may also comprise ceramic material as discussed above in the first embodiment, and/or growth factors, antioxidants, autograft and allograft material, stem cells and cell therapies, drugs, DNA and RNA based therapies and antibodies as discussed above in the first embodiment.

The above described additional components of the gel may be present in the gel in any amount that will allow the added component to have a beneficial effect on enhancing bone growth and/or providing improved physical stability or handling characteristics, while not significantly altering the stability or form of the gel material.

As noted above, the gel of the fifth embodiment is a suitable carrier for demineralized bone matrix. Demineralized bone is preferably added to the gel of the fifth embodiment in an amount of up to 0.55 grams per 1 gram of gel, and is preferably added at a rate of 0.3 grams per 1 gram of gel. After adding an appropriate amount of DBM to the gel of the fifth embodiment, the gel is suitably injectable so that the delivery of the DBM to the defect site is achieved with greater ease.

In a sixth embodiment of the present invention, an emulsion for use as a bone void filler and which is also a suitable DBM carrier is disclosed. The emulsion comprises soluble keratin protein suspended in oil.

The keratin component of the emulsion is identical to the keratin described above with respect to the putty and gel. That is to say, the emulsion comprises soluble keratin protein, which may be S-sulfonated, oxidized, or reduced keratin and the soluble keratin is preferably intact keratin protein fraction, such as intact intermediate filament keratin protein.

As described above with respect to the putty and gel, the soluble keratin protein of the emulsion is preferably in a solution, the solution being any suitable solution for use in a bone void filler, such as water. The aqueous solution may be any ratio of soluble keratin to solution suitable for preparing an aqueous solution.

Prior to being added to the oil component of the emulsion, insoluble keratin may be further added to the aqueous solution of soluble keratin protein to regulate the viscosity prior to sterilization. Crosslinked S-sulfonated keratin or lanthionized keratin are two types of insoluble keratin which may be used.

Also as described in detail above, the emulsion may further comprise additional components to improve the handling characteristics of the emulsion and/or bone enhancement. Thus, as with the putty and gel, the emulsion may further comprise plasticizers, ceramic material, antioxidants, autograft, allograft, cell therapies, stem cells, drugs, DNA-based therapies, RNA-based therapies, antibodies, and/or preservatives.

Prior to mixing the aqueous solution of soluble keratin protein in the oil, demineralized bone matrix may be added to the aqueous solution. The oil component of the emulsion may comprise any suitable oil, for example, castor oil or mineral oil.

In a seventh embodiment of the present invention, a method for preparing a putty for use as bone void filler is disclosed. The method generally comprises preparing an aqueous solution of soluble keratin protein and then mixing the aqueous solution with insoluble keratin to form a putty.

The keratin is soluble keratin as described previously. The aqueous solution of keratin protein may be prepared in any manner suitable for preparing an aqueous solution, including addition of soluble keratin to a solution such as water. The aqueous solution may be any ratio of soluble keratin to solution suitable for preparing an aqueous solution and the aqueous solution may take the formation of a gel. In a preferred aspect of the seventh embodiment, the soluble keratin is 4-25% by weight of the final putty and the water is 20-40% by weight of the final putty. In a most preferred aspect of the seventh embodiment, the soluble keratin is 13.5% by weight of the final putty and the water is 29.4% by weight of the final putty.

The gel may then be mixed with insoluble keratin to form a putty. When mixing the gel with insoluble keratin, the insoluble keratin is preferably cross-linked S-sulfonated keratin or lanthionized keratin and is from 15-50% by weight of the final putty. More preferably, the insoluble keratin is 45.1% by weight of the final putty.

The insoluble keratin may be added to the aqueous solution by any means suitable. The mixing of the aqueous solution of S-sulfonated keratin protein and insoluble keratin may be by any means suitable for mixing or blending. For example, mixing of the two components may be by using a stirrer and mixing the components by hand.

The step of mixing the insoluble keratin and soluble keratin protein solution of the seventh embodiment may also include the addition of additional components as described above in previous embodiments. For example, plasticizer in the range of 0-3% by weight of the putty may be added (most preferably 1.5%), ceramic in the range of 0-15% by weight of the putty may be added (most preferably 10%), and preservative in the range of 0 to 1% by weight of the putty may be added (most preferably 0.5%).

Once insoluble keratin has been added and mixed to form the putty, a final step of adding autologous bone chips to the putty prior to application to the bone void may be conducted. The bone chips are preferably added to the putty in the range of up to 0.5 grams of bone chips per 1 gram of putty. The bone chips may be mixed with the putty using any means known for mixing.

In an eighth embodiment of the present invention, a method for preparing a gel for use as a bone void filler is disclosed. The method generally comprises preparing an aqueous solution of soluble keratin protein and then mixing the aqueous solution with insoluble keratin to form a gel.

The keratin is soluble keratin as described previously. The aqueous solution of keratin protein may be prepared in any manner suitable for preparing an aqueous solution, including addition of soluble keratin to a solution such as water. The aqueous solution may be any ratio of soluble keratin to solution suitable for preparing an aqueous solution and the aqueous solution may take the formation of a gel. In a preferred aspect of the eighth embodiment, the soluble keratin is 4-25% by weight of the final gel and the water is 20-50% by weight of the final gel.

The gel may then be mixed with insoluble keratin to form a putty. When added to the gel, the insoluble keratin is preferably cross-linked S-sulfonated keratin or lanthionized keratin and is from 20-50% by weight of the final gel.

The insoluble keratin may be added to the aqueous solution by any means suitable. The mixing of the aqueous solution of S-sulfonated keratin protein and insoluble keratin may be by any means suitable for mixing or blending. For example, mixing of the two components may be by using a stirrer and mixing the components by hand.

The step of mixing the insoluble keratin and soluble keratin protein solution of the eighth embodiment may also include the addition of additional components as described above in previous embodiments. For example, plasticizer in the range of 0-3% by weight of the gel may be added, ceramic in the range of 0-15% by weight of the gel may be added, and preservative in the range of 0 to 1% by weight of the gel may be added.

Once insoluble keratin has been added and mixed to form the gel, a final step of adding autologous bone chips to the gel prior to application to the bone void may be conducted. The autologous bone chips are preferably added to the gel in the range of up to 0.5 grams of bone chips per 1 gram of gel. The bone chips may be mixed with the gel using any means known for mixing.

In a ninth embodiment of the present invention, a method for preparing an emulsion for use as a bone void filler is disclosed. The method generally comprises preparing an aqueous solution of soluble keratin protein and then mixing the aqueous solution with oil to form an emulsion. Examples of oils suitable for use in the emulsion include, but are not limited to, castor oil and mineral oil The keratin is soluble keratin as described previously. The aqueous solution of keratin protein may be prepared in any manner suitable for preparing an aqueous solution, including addition of soluble keratin to a solution such as water. The aqueous solution may be any ratio of soluble keratin to solution suitable for preparing an aqueous solution.

Prior to mixing the keratin solution with oil to form an emulsion, additional components as described in previous embodiments may be added to the aqueous solution. For example, growth factors as described above may be mixed with the aqueous solution.

The soluble keratin protein solution is then mixed with oil to form an emulsion.

The oil may be added to the aqueous solution by any means suitable. The mixing of the aqueous solution of S-sulfonated keratin protein and oil may be by any means suitable for mixing or blending. For example, mixing of the two components may be by using a stirrer and mixing the components by hand.

In a tenth embodiment of the present invention, a method for preparing a putty for use as bone void filler and which is a suitable carrier for demineralized bone matrix is disclosed. The method generally comprises preparing an aqueous solution of soluble keratin protein and then mixing the aqueous solution with insoluble keratin to form a putty.

The keratin is soluble keratin as described previously. The aqueous solution of keratin protein may be prepared in any manner suitable for preparing an aqueous solution, including addition of soluble keratin to a solution such as water. The aqueous solution may be any ratio of soluble keratin to solution suitable for preparing an aqueous solution and the aqueous solution may take the formation of a gel. In a preferred aspect of the tenth embodiment, the soluble keratin is 15-45% by weight of the final putty and the water is 25-75% by weight of the final putty. In a most preferred aspect of the tenth embodiment, the soluble keratin is 28.1% by weight of the final putty and the water is 66% by weight of the final putty.

The gel may then be mixed with insoluble keratin to form a putty. When adding insoluble keratin, the insoluble keratin is preferably cross-linked S-sulfonated keratin or lanthionized keratin and is from 0-5% by weight of the final putty. More preferably, the insoluble keratin is 1.9% by weight of the final putty.

The insoluble keratin may be added to the aqueous solution by any means suitable. The mixing of the aqueous solution of S-sulfonated keratin protein and insoluble keratin may be by any means suitable for mixing or blending. For example, mixing of the two components may be by using a stirrer and mixing the components by hand.

The step of mixing the insoluble keratin and soluble keratin protein solution of the tenth embodiment may also include the addition of additional components as described above in previous embodiments. For example, plasticizer in the range of 0-5% by weight of the putty may be added (most preferably 3%), and preservative in the range of 0 to 1% by weight of the putty may be added (most preferably 1%).

Once insoluble keratin has been added and mixed to form the putty, a final step of adding demineralized bone matrix to the putty prior to application to the bone void may be conducted. The DBM is preferably added to the putty in the range of up to 0.55 grams of DBM per 1 gram of putty, and is more preferably added to the putty at a rate of 0.3 grams per 1 gram of putty. The DBM may be mixed with the putty using any means known for mixing.

In a eleventh embodiment of the present invention, a method for preparing a gel for use as bone void filler and which is a suitable carrier for demineralized bone matrix is disclosed. The method generally comprises preparing an aqueous solution of soluble keratin protein and then mixing the aqueous solution with insoluble keratin to form a gel.

The keratin is soluble keratin as described previously. The aqueous solution of keratin protein may be prepared in any manner suitable for preparing an aqueous solution, including addition of soluble keratin to a solution such as water. The aqueous solution may be any ratio of soluble keratin to solution suitable for preparing an aqueous solution and the aqueous solution may take the formation of a gel. In a preferred aspect of the eleventh embodiment, the soluble keratin is 10-35% by weight of the final gel and the water is 30-80% by weight of the final gel. In a most preferred aspect of the eleventh embodiment, the soluble keratin is 21.3% by weight of the final gel and the water is 72.8% by weight of the final gel.

The gel may then be mixed with insoluble keratin to form a final gel. When insoluble keratin is mixed with the gel, the insoluble keratin is preferably cross-linked S-sulfonated keratin or lanthionized keratin and is from 0-5% by weight of the final gel. More preferably, the insoluble keratin is 1.9% by weight of the final gel.

The insoluble keratin may be added to the aqueous solution by any means suitable. The mixing of the aqueous solution of S-sulfonated keratin protein and insoluble keratin may be by any means suitable for mixing or blending. For example, mixing of the two components may be by using a stirrer and mixing the components by hand.

The step of mixing the insoluble keratin and soluble keratin protein solution of the eleventh embodiment may also include the addition of additional components as described above in previous embodiments. For example, plasticizer in the range of 0-5% by weight of the putty may be added (most preferably 3%), and preservative in the range of 0 to 1% by weight of the putty may be added (most preferably 1%).

Once insoluble keratin has been added and mixed to form the putty, a final step of adding demineralized bone matrix to the putty prior to application to the bone void may be conducted. The DBM is preferably added to the putty in the range of up to 0.55 grams of DBM per 1 gram of putty, and is more preferably added at a rate of 0.3 grams per 1 gram of gel. The DBM may be mixed with the putty using any means known for mixing.

In a twelfth embodiment of the present invention, a method for preparing an emulsion for use as a bone void filler and which is suitable as a carrier for demineralized bone matrix is disclosed. The method generally comprises preparing an aqueous solution of soluble keratin protein and then mixing the aqueous solution with oil to form an emulsion. Examples of oils suitable for use in the emulsion include, but are not limited to, castor oil and mineral oil.

The keratin is soluble keratin as described previously. The aqueous solution of keratin protein may be prepared in any manner suitable for preparing an aqueous solution, including addition of soluble keratin to a solution such as water. The aqueous solution may be any ratio of soluble keratin to solution suitable for preparing an aqueous solution.

Prior to mixing the keratin solution with oil to form an emulsion, additional components as described in previous embodiments may be added to the aqueous solution. For example, growth factors as described above may be mixed with the aqueous solution.

Further, the aqueous solution may be mixed with demineralized bone matrix prior to mixing the solution with oil to create the emulsion.

The soluble keratin protein solution is then mixed with oil to form an emulsion.

The oil may be added to the aqueous solution by any means suitable. The mixing of the aqueous solution of S-sulfonated keratin protein and oil may be by any means suitable for mixing or blending. For example, mixing of the two components may be by using a stirrer and mixing the components by hand.

WORKING EXAMPLES

Formulation of Bone-Void Filling Putties

Example 1a 13.5% by weight of oxidized keratin powder is mixed with 29.5% by weight of water to form an aqueous solution. 45% by weight of cross-linked keratin powder, 10% by weight calcium phosphate, 1.5% by weight glycerol and 0.5% by weight of preservative (paraben+phenoxyethanol mix) is mixed in the aqueous solution to form a bone-void filling putty. 0.5 grams of bone chips per 1 gram of putty is added to the putty prior to insertion in a bone void.

Example 1b)

15% by weight of oxidized keratin powder is mixed with 33% by weight of water to form an aqueous solution. 40% by weight of cross-linked keratin powder, 10% by weight calcium phosphate, 1.5% by weight glycerol and 0.5% by weight of preservative (paraben+phenoxyethanol mix) is mixed in the aqueous solution to form a bone-void filling putty. 0.5 grams of bone chips per 1 gram of putty is added to the putty prior to insertion in a bone void.

Example 1c)

12% by weight of oxidized keratin powder is mixed with 26% by weight of water to form an aqueous solution. 50% by weight of cross-linked keratin powder, 10% by weight calcium phosphate, 1.5% by weight glycerol and 0.5% by weight of preservative (paraben+phenoxyethanol mix) is mixed in the aqueous solution to form a bone-void filling putty. 0.5 grams of bone chips per 1 gram of putty is added to the putty prior to insertion in a bone void.

Formulation of Demineralized Bone Matrix Carrier Putties

Example 2a)

29.1% by weight of oxidized keratin powder is mixed with 67.9% by weight of water to form an aqueous solution. 2% by weight of cross-linked keratin powder and 1% by weight of preservative (paraben+phenoxyethanol mix) is mixed in the aqueous solution to form a bone-void filling putty. 0.3 grams of demineralized bone matrix per 1 gram of putty is added to the putty prior to insertion in a bone void.

Example 2b)

28.1% by weight of oxidized keratin powder is mixed with 65.9% by weight of water to form an aqueous solution. 2% by weight of cross-linked keratin powder, 3% by weight glycerol, and 1% by weight of preservative (paraben+phenoxyethanol mix) is mixed in the aqueous solution to form a bone-void filling putty. 0.3 grams of demineralized bone matrix per 1 gram of putty is added to the putty prior to insertion in a bone void.

Formulation of Demineralized Bone Matrix Carrier Gels

Example 3a)

21.3% by weight of oxidized keratin powder is mixed with 72.8% by weight of water to form an aqueous solution. 1.9% by weight of cross-linked keratin powder, 3% by weight glycerol and 1% by weight of preservative (paraben+phenoxyethanol mix) is mixed in the aqueous solution to form a bone-void filling gel. 0.3 grams of demineralized bone matrix per 1 gram of putty is added to the gel prior to insertion in a bone void.

Example 3b)

22% by weight of oxidized keratin powder is mixed with 75% by weight of water to form an aqueous solution. 2% by weight of cross-linked keratin powder and 1% by weight of preservative (paraben+phenoxyethanol mix) is mixed in the aqueous solution to form a bone-void filling gel. 0.3 grams of demineralized bone matrix per 1 gram of gel is added to the gel prior to insertion in a bone void.

What we claimed is:

1. A bone-void filling putty or gel, comprising: soluble keratin protein, wherein the soluble keratin protein is a keratin protein fraction, and insoluble keratin protein.

2. The bone-void filling putty or gel of claim 1, wherein the keratin protein fraction is selected from the group consisting of intermediate filament protein, high sulfur protein and high glycine-tyrosine protein.

3. A bone-void filling putty or gel, comprising: soluble keratin protein, insoluble keratin protein, and a plasticizer.

4. A bone-void filling putty or gel, comprising: soluble keratin protein, insoluble keratin protein, and autologous bone chips.

5. The bone-void filling putty or gel of claim 4, wherein the putty or gel comprises less than 0.5 grams of bone chips per one gram of putty or gel.

6. A bone-void filling putty or gel, comprising: soluble keratin protein, insoluble keratin protein, and ceramic material.

7. A bone-void filling putty or gel, suitable for carrying demineralized bone matrix, comprising: 10-40% by weight soluble keratin protein, wherein the soluble keratin protein is a keratin protein fraction, 25-80% by weight water, and 1.9-5% by weight insoluble keratin protein.

8. The bone-void filling putty or gel of claim 7, wherein the keratin protein fraction is selected from the group consisting of intermediate filament protein, high sulfur protein and high glycine-tyrosine protein.

9. A bone-void filling putty or gel, suitable for carrying demineralized bone matrix, comprising: 10-40% by weight soluble keratin protein, 25-80% by weight water, 1.9-5% by weight insoluble keratin protein, and 0-5% by weight plasticizer.

10. A bone-void filling putty or gel, suitable for carrying demineralized bone matrix, comprising: 10-40% by weight soluble keratin protein, 25-80% by weight water, 1.9-5% by weight insoluble keratin protein, and demineralized bone matrix.

11. The bone-void filling putty or gel of claim 10, wherein the putty or gel comprises less than 0.55 grams of demineralized bone matrix per one gram of putty or gel.

12. A method for preparing a putty or gel for use as a bone-void filler comprising the steps of:
    a) preparing an aqueous solution of soluble keratin protein; and
    b) mixing the aqueous solution of keratin protein with insoluble keratin protein to form a putty or gel.

13. The method of claim 12, further comprising the step of mixing the putty or gel with autologous bone chips.

14. The method of claim 12, further comprising the step of mixing the putty or gel with demineralized bone matrix.

15. A bone-void filling putty or gel, comprising: 4-45 weight % water soluble oxidized keratin protein, 20-80 weight % water, and 1.9-60 weight % water-insoluble cross-linked S-sulfonated keratin protein, wherein the water-insoluble cross-linked S-sulfonated keratin protein consists essentially of intermediate filament protein.

16. A bone-void filling putty or gel, comprising: 4-45 weight % water soluble oxidized keratin protein, 20-80 weight % water, and 1.9-60 weight % water-insoluble cross-linked S-sulfonated keratin protein, further comprising a plasticizer, autologous bone chips, a ceramic, or a combination thereof.

17. The bone-void filling putty or gel of claim 15, further comprising a plasticizer, autologous bone chips, a ceramic, or a combination thereof.

* * * * *